United States Patent [19]

Yoneyama

[11] 4,338,398

[45] Jul. 6, 1982

[54] IMMOBILIZATION OF STARCH DEGRADING ENZYMES

[75] Inventor: Masaru Yoneyama, Souja, Japan

[73] Assignee: Kabushiki Kaisha Hayashibara Seibutsu Kagaku Kenkyujo, Okayama, Japan

[21] Appl. No.: 130,182

[22] Filed: Mar. 13, 1980

[30] Foreign Application Priority Data

Mar. 20, 1979 [JP] Japan .................................. 54-32874
Jan. 12, 1980 [JP] Japan .................................. 55-2316

[51] Int. Cl.³ ...................... C12P 19/22; C12N 11/00
[52] U.S. Cl. ........................................ 435/95; 435/96; 435/99; 435/174; 435/178; 435/179; 435/180; 435/188; C12N/11/08
[58] Field of Search ............... 435/174, 176, 178, 179, 435/177, 180, 181, 182, 95, 96–99, 188

[56] References Cited

U.S. PATENT DOCUMENTS

| | | | |
|---|---|---|---|
| 3,654,083 | 4/1972 | Moelker | 435/177 |
| 3,691,016 | 9/1972 | Patel | 435/181 |
| 3,705,084 | 12/1972 | Reynolds | 435/182 X |
| 3,969,287 | 7/1976 | Jamorek et al. | 435/181 X |
| 4,121,974 | 10/1978 | Hofreiter et al. | 435/181 X |
| 4,226,937 | 10/1980 | Abdullah et al. | 435/96 |
| 4,254,227 | 3/1981 | Okada et al. | 435/97 |

OTHER PUBLICATIONS

Vieth, et al., "Enzyme Engineering, Part II, Materials for Immobilized Enzyme Reactors", *Chemtech*, Jan. 1974, pp. 47–55.

*Primary Examiner*—David M. Naff
*Attorney, Agent, or Firm*—Browdy and Neimark

[57] ABSTRACT

Starch degrading enzymes are immobilized by modifying or cross-linking the starch-degrading enzymes with a mono- or poly-functional reagent in a manner that does not substantially insolubilize the enzymes and then physically adsorbing the resultant modified or cross-linked enzymes onto a water-insoluble carrier. The resultant immobilized enzymes have high activity and the carrier can be easily recovered for repeated use.

10 Claims, No Drawings

IMMOBILIZATION OF STARCH DEGRADING ENZYMES

DETAILED DESCRIPTION OF THE INVENTION

The present invention relates to processes for preparing immobilized enzyme, particularly immobilized-starch-degrading enzyme, and a reaction product with said immobilized enzyme.

Immobilized enzymes, or insolubilized enzymes, have been prepared by various techniques such as covalent binding, entrapping and cross-linking. No large-scale production of immobilized-starch-degrading enzyme has, however, been carried out and no immobilized-starch-degrading enzyme has been used to produce reaction products from amylaceous material because its residual activity after immobilization is generally low due to the retrogradation of the amylaceous substrate solution containing high molecular-weight substances and/or the requirement of high concentration in the substrate solution.

The present inventor investigated processes for preparing immobilized-starch-degrading enzyme and the reaction product with said immobilized enzyme. The efforts resulted in the present invention that differs from conventional immobilization processes involving direct coupling of native enzyme protein and offers a method for preparing an immobilized-starch-degrading enzyme of high starch-degrading activity by modifying in solution a starch-degrading enzyme with a modifying reagent in a manner that the enzyme is not insolubilized substantially, and then adsorbing the modified enzyme onto a carrier. The present invention is also based on the finding that industrial production of the reaction product therewith can be easily performed by subjecting a substrate solution containing amylaceous material to the action of said immobilized enzyme.

Employable starch-degrading enzymes in the invention include cyclodextrin glucanotransferase (E.C. 2.4.1.19) which transfers glycosyl residue of starch or a partial starch hydrolysate, and α-amylase (E.C. 3.2.1.1), β-amylase (E.C. 3.2.1.2), glucoamylase (E.C. 3.2.1.3), pullulanase (E.C. 3.2.1.41) and isoamylase (E.C. 3.2.1.68) which hydrolyze glucosidic linkages. Usable enzyme preparations in the present invention are chosen from a group comprising crude enzymes of microorganisms, animals and plants, and their purified and partially-purified preparations.

Usable modifying reagents are those which cross-link and/or modify starch-degrading enzyme protein in a manner that the enzyme is not insolubilized substantially by the modification reaction without unnecessary enzyme inactivation, and which have one or more functional groups that react with certain group(s) of the enzyme protein. Functional groups reactive with certain group(s) of the enzyme protein include diazo, carboxyl, acid anhydride, acid azide, acid halide, isocyanate, isothiocyanate, carbodiimide, imidocarbonate, thioamide, maleimide, formyl, methylol, halogen and sulfonylchloride groups.

Usable mono-functional reagents in the invention include mono-aldehyde compounds such as acetaldehyde, propionaldehyde, butyraldehyde, octyl aldehyde, lauraldehyde, oleyl aldehyde, benzaldehyde, p-nitrobenzaldehyde and naphthaldehyde, and acylating agents such as succinic anhydride, maleic anhydride and N-acetoxy-succinimide. When the latter reagent is used, an acetyl group can be introduced into the enzyme protein by treating the enzyme with a water-soluble carbodiimide instead of N-acetoxy-succinimide in the presence of acetic acid.

Usable bi-functional reagents include diisocyanate compounds such as hexamethylene diisocyanate and toluene 2,4-diisocyanate, dialdehyde compounds such as glyoxal, glutaraldehyde and succindialdehyde, and diazo compounds such as bis-azo-benzidine. In addition to the above-described reagents, N,N'-ethylene-bis-maleimide and water-soluble carbodiimides are also feasible in the present invention.

Usable poly-functional reagents in the present invention include cyanuric chloride, dialdehyde starch and dialdehyde pullulan.

In respect to the reaction conditions, any conditions can be applied as far as they do not cause unnecessary enzyme inactivation during modification reaction, and effect the reaction in a manner that the enzyme is not insolubilized substantially. Generally the following conditions stable for enzyme are preferable: the modification reaction should be carried out in a manner such that the enzyme is not insolubilized substantially with a starch-degrading enzyme solution, concentration about 0.01 to 5 w/v %, and a modifying reagent, concentration about 0.001 to 5 w/v %, at a pH in the range of about 3 to 10 and a temperature in the range of about 0° to 80° C. for 0.1 to 50 hours. In this case a sufficient amount of enzyme stabilizers such as substrate or salt may be added to prevent enzyme inactivation during the modification.

Modifying a starch-degrading enzyme in a manner that the enzyme is not insolubilized substantially, referred to in the present invention, means that the modification reaction is suspended at a level where the reaction mixture containing the modified enzyme appears transparent or slightly cloudy.

Usable carriers in the present invention include activated carbon, porous glass, Japanese acid clay, bleaching clay, kaolinite, alumina, silica gel, bentonite, ceramics, hydroxylapatite, calcium phosphate gel, starch, amylose, pullulan, dextran, cellulose, porous co-polymer resins, and their derivatives.

Preferable porous co-polymer resins are those which are non-ionic and able to adsorb enzyme protein, and which are synthesized by co-polymerizing styrene monomer and methyl styrene, nitrostyrene, styryl halide, acrylonitrile, vinyl acetate, vinyl chloride, divinylbenzene, butadiene or isopurene monomer. Suitable commercialized co-polymer resins are Amberlite XAD-1, XAD-2, XAD-4, XAD-7, XAD-8, XAD-9, XAD-11 and XAD-12 (Registered Trade Marks of Rohm & Haas Co., Philadelphia, Pa., U.S.A.); Diaion HP-10, HP-20, HP-30, HP-40 and HP-50 (Registered Trade Marks of Mitsubishi Chemical Industries Ltd., Tanashi, Tokyo, Japan); and Imac Syn-42, Syn-44 and Syn-46 (Registered Trade Marks of Industrie de Maatshappily activate N.V., Amsterdam, Netherlands).

In order to adsorb and immobilize a starch-degrading enzyme, which is modified in a manner that the enzyme is not insolubilized substantially, to any of the above-described carriers, a reaction mixture containing the modified enzyme, but preferablly a solution containing the modified enzyme, should be contacted with the carrier after dialyzing and/or salting out the modified enzyme to remove an excess unreacted modifying reagent.

As to procedures for contacting modified starch-degrading enzyme with carrier, any procedures can be employed as far as the modified enzyme is absorbed and immobilized thereby onto the carrier without unnecessary enzyme inactivation: for example, adding a carrier in a solution containing modified enzyme, or packing a carrier in a column and then passing the solution through the column to adsorb and immobilize the modified enzyme.

The fact that the adsorbed-starch-degrading enzyme content is in the range of about 0.001 to 50 w/w % d.s.b., and particularly that the amount is easily increased to about 1 w/w % d.s.b. or more when a porous co-polymer resin used, enable an attainment of immobilized enzyme having an extremely high specific acitivity.

The immobilized-starch-degrading enzyme thus obtained is usually used under the following enzymatically active industrial conditions: allowing an amylaceous substrate solution comprising starch or partial starch hydrolysate, concentration about 5 to 50 w/w % and D.E. about below 70, to contact with the immobilized-starch-degrading enzyme at a pH, about 3 to 10, and a temperature, about 20° to 80° C., for about 0.1 to 1,000 hours.

Although the modified enzyme is bound physically when the immobilized enzyme is prepared according to the invention, the adsorption force is very strong, and thus no leakage of the adsorbed enzyme from the carrier is observed even during reaction using a high concentration substrate solution.

As to mode for immobilized-enzyme-reactor operation, a continuous operation with a column system, and a batch-wise system wherein the recovery of the immobilized enzyme is much easier, are both employable in the invention.

Since the thermal- and pH-stabilities of the immobilized-starch-degrading enzyme prepared according to the invention are considerably enhanced by immobilization in comparison with those of the native enzyme, and their half lives range from several tens hours to several hundreds hours, the immobilized-starch-degrading enzyme can be advantageously used in the commercial production of reaction products from amylaceous materials.

Furthermore, carrier can be recovered easily and used repeatedly. When the immobilized enzyme is contaminated with various microbes and its activity decreases, the carrier can be easily recovered because the contaminants such as proteinaceous substances are easily removed from the reactor system by washing the immobilized enzyme with polar solvents such as acetone, methanol or ethanol, or with an alkali or acid solution in a concentration of about 0.1 to 5 N. The recovered resin can be, of course, used repeatedly as carrier to immobilize enzyme.

EXPERIMENTs below describe immobilized-starch-degrading enzyme prepared according to the present invention.

EXPERIMENT

Experiment 1

Preparation of a Starch-degrading Enzyme

To 1,500 liters of a sterilized liquid medium comprising 2.5 w/v % soluble starch, 0.5 w/v % corn steep liquor, 0.3 w/v % ammonium nitrate, 0.1 w/v % $K_2HPO_4$, 0.05 w/v % $MgSO_4.7H_2O$ and 0.5 w/v % $CaCO_3$ was inoculated Bacillus stearothermophilus TC-91, FERM-P No. 2225, and the mixture was cultured at 50° C. for 72 hours under agitating and aerobic conditions. The culture broth was then centrifuged to obtain a supernatant having a cyclodextrin glucanotransferase activity (glucosidic transferase activity) of 120 units per ml as defined by the assay method described hereafter. The supernatant was cooled to 4° C. and the enzyme in the supernatant was salted out by the addition of ammonium sulfate to 60% saturation. Then the resulting precipitate was collected. The collected precipitate was dissolved in a small amount of water, dialyzed against water overnight, and then lyophilized into powder. The powder precipitate thus obtained had a specific activity of about 230 units per mg protein and the total activity recovery was about 80% against that in the supernatant of the culture broth.

Cyclodextrin glucanotransferase activity (glucosidic transferase activity) was assayed as follows:

To 2 ml of a 1 w/w % α-cyclodextrin solution is added 2 ml of a 2.5 w/w % sucrose solution and a given amount of enzyme solution to give a final volume of 4.5 ml. The mixture is incubated at 40° C. for a given period of time, and 0.5 ml of the reaction mixture is sampled. Then the reaction mixture is added with 0.1 ml of a solution containing commercial glucoamylase, 5 units, and is incubated at this temperature for an additional 1 hour to decompose all the α-1,4-linkage oligosaccharides excluding α-cyclodextrin into glucose. The release glucose is determined by the Somogyi-Nelson method.

One unit of cyclodextrin glucanotransferase activity is defined as the amount of enzyme that hydrolyzes 1μ mole of α-cyclodextrin per minute under the above conditions.

Experiment 2

Modification of a Starch-degrading Enzyme

A powder cyclodextrin glucanotransferase prepared by the method as described in EXPERIMENT 1 was dissolved in a 0.05 M acetate buffer, pH 6.0, containing 0.02 M calcium chloride to give a starch-degrading enzyme solution having a protein concentration of 0.2 w/v %. To 4 ml aliquots of the above solution were added an aqueous glutaraldehyde solution to give respective concentration of 1, 5, 10, 20, 50, 80, 100, 150 and 200 w/w % per protein, and the resulting solutions were then subjected to modification reaction at room temperature for 1 hour while stirring gently. Then the reaction mixtures were dialyzed against water for an additional 5 hours to remove excess unreacted glutaraldehyde, and the activities of the dialyzed solutions were assayed to determine the activity recoveries (%) against that of the starting native enzyme. The results are shown in Line A of the TABLE. Control experiment was carried out similarly except that the aqueous glutaraldehyde solution was replaced with water. The appearances of the solutions containing modified enzyme are described in Line B of the TABLE.

Experiment 3

Immobilization of a Modified Starch-degrading Enzyme

To each dialyzed modified enzyme solution prepared in EXPERIMENT 2 was added 1 g wet weight of Diaion HP-20 as a carrier to adsorb the modified enzyme and to prepare immobilized-starch-degrading enzyme. The non-adsorbed activities were assayed and the immobilization efficiencies (%) of each system were determined. The results are shown in Line C of the TABLE. The apparent activities of the immobilized-starch-degrading enzymes were assayed and the activity yields (%) against that of the starting native enzyme were determined. The results are shown in Line D of the TABLE.

As obvious from the results shown in the TABLE, in order to prepare an immobilized-starch-degrading enzyme having a high apparent activity, it is required that a starch-degrading enzyme be modified in a manner that the enzyme is not insolubilized substantially, but is adsorbed and immobilized onto carrier. Although a native enzyme immobilized similarly attained an immobilization efficiency of 100%, only a much less apparent activity of the resulting immobilized enzyme was detected. Furthermore, augmentation of the modification reaction to a level where the enzyme is insolubilized substantially decreased the activity yield, and halved the immobilization efficiency. Consequently, the apparent activity of the resulting immobilized enzyme was reduced extremely.

TABLE

| a' (w/v %) | 0 | 0.004 | 0.02 | 0.04 | 0.08 | 0.2 | 0.32 | 0.4 | 0.6 | 0.8 |
|---|---|---|---|---|---|---|---|---|---|---|
| b' (w/w %) | 0 | 1 | 5 | 10 | 20 | 50 | 80 | 100 | 150 | 200 |
| A (%) | 100 | 100 | 100 | 98 | 95 | 90 | 86 | 73 | 41 | 19 |
| B | | | Transparent | | | | | Slightly cloudy | | White precipitate occurred |
| C (%) | 100 | 100 | 100 | 97 | 95 | 93 | 91 | 89 | 76 | 53 |
| D (%) | 1.6 | 38 | 64 | 73 | 81 | 78 | 75 | 61 | 29 | 8.2 | where a' (w/v %) is the glutaraldehyde concentration (w/v %), b' (w/w %) is the amount of glutaraldehyde added per enzyme protein (w/w %), A (%) is the activity yield (%) of the modified and dialyzed enzyme, B is the appearance of the solution containing the modified and dialyzed enzyme, C (%) is the immobilization efficiency of the modified and dialyzed enzyme tested;

Immobilization efficiency (%) =
$$\frac{\text{(Total activity before adsorption)} - \text{(Activity in supernatant)}}{\text{Total activity before adsorption}} \times 100$$

and D (%) is the activity yield of the immobilized enzyme against that of the starting native enzyme.

In order to modify a starch-degrading enzyme in a manner that the enzyme is not insolubilized substantially, an equi- or much less amount of modifying reagent should be used, depending upon the reaction conditions such as protein concentration, reaction temperature and reaction time.

Several embodiments according to the present invention are described below.

EXAMPLE 1

Immobilized Cyclodextrin Glucanotransferase

A powder Bacillus cyclodextrin glucanotransferase prepared by the method as described in EXPERIMENT 1 was dissolved in 0.05 M acetate buffer, pH 6.0, containing 2 mM calcium chloride, to give a 0.4 w/v % enzyme solution. To 100 ml of the solution was added an aqueous glutaraldehyde solution to give a concentration of 0.05 w/v %, and the resulting mixture was kept at room temperature for 2 hours to effect modification reaction. Then to the reaction mixture was added 10 g wet weight of Diaion HP-30 to adsorb the modified enzyme, and the resultant was washed with water to obtain an immobilized cyclodextrin glucanotransferase.

The overall activity yield of the immobilized enzyme thus obtained was about 77% against that of the starting enzyme.

The immobilized cyclodextrin glucanotransferase was feasible for various applications. For example it is advantageously feasible for producing cyclodextrin or various sugars such as glycosylsucrose, glycosyllactose, glycosylriboflavin, glycosylesculin, glycosylrutin and glycosylstevioside from respective mixtures of partial starch hydrolysate and a member of a group consisting of sugar-acceptor sucrose, lactose, riboflavin, esculin, rutin and stevioside. In these cases, the half life of the immobilized cyclodextrin glucanotransferase at a reaction temperature of about 60° C. was about 800 hours.

EXAMPLE 2

Immobilized α-amylase

A commercial Aspergillus α-amylase DENAZYME (Registered Trade Mark of Nagase & Co., Ltd., Osaka, Japan) was dissolved in water to give a protein concentration of 0.15 w/v %. To 50 ml of the solution was added 2 ml of 1 M acetate buffer, pH 6.0, containing 300 mg of 1-cyclohexyl-3-(2-morpholinoethyl) carbodiimide metho-p-toluene sulfonate, and the resulting solution was kept at room temperature for 4 hours, and dialyzed against water for an additional 5 hours. The dialyzed modified enzyme solution was added with 5 g wet weight of Amberlite XAD-1, and the mixture was stirred gently overnight at this temperature to obtain an immobilized α-amylase.

The overall activity yield against that of the starting native enzyme was about 60%. In this case the enzyme activity was assayed as follows:

To 2 ml of a substrate solution consisting of a 0.1 M acetate buffer, pH 6.0, and a partially acid-hydrolyzed waxy corn starch, concentration 5 w/w % and D.E. 50, is added a given amount of enzyme to give a final volume of 2.5 ml. Then the mixture is incubated at 40° C. for 10 minutes to effect enzymatic reaction. The release sugars are assayed as glucose according to the Somogyi-Nelson method.

One unit of enzyme activity is defined as the amount of enzyme that produces 1μ mole of reducing sugars as glucose per minute under the above conditions.

The immobilized α-amylase thus obtained was feasible for various applications. For example the product is suitable in the production of corn syrup, glucose or maltose from amylaceous material, exhibiting a half life of about 400 hours at a reaction temperature of about 60° C.

EXAMPLE 3

Immobilized β-amylase

A β-amylase preparation, extracted from defatted soybeans and salted out according to conventional methods, was dissolved in a 0.5 M phosphate buffer, pH 7.0, containing 0.01 M maltose, to give a protein concentration of 0.1 w/v %. To 50 ml of the solution was added 20 ml of a 0.1 w/v % acetone solution of cyanuric chloride, and the mixture was kept for 3 hours at 4° C. while preventing pH-decrease, and then dialyzed against water for an additional 5 hours. To the reaction mixture was added 5 g wet weight of Diaion HP-10, and the resulting admixture was stirred gently at 4° C. overnight to obtain an immobilized β-amylase.

The overall activity yield of the immobilized enzyme was about 68% against that of the starting native enzyme. The enzyme activity was assayed similarly as in EXAMPLE 2.

The immobilized β-amylase was feasible for various applications. Particularly, it is suitable for producing high maltose syrup or maltose from amylaceous material, exhibiting a half life of about 200 hours at a reaction temperature of about 50° C.

EXAMPLE 4

Immobilized Glucoamylase

A commercial Aspergillus glucoamylase XL-128 (Registered Trade Mark of Nagase & Co., Ltd., Osaka, Japan) was diluted with a 0.02 M acetate buffer, pH 5.0, to give a protein concentration of 0.15 w/v %. To 50 ml of the solution was added 20 ml of a 0.3 w/v % dioxane solution of toluene 2,4-diisocyanate, and the resulting solution was kept overnight at 4° C., and then dialyzed against water for an additional 5 hours. Then the solution containing modified enzyme was added with 5 g wet weight of Imac Syn-46, stirred gently overnight at 4° C., and the resultant was washed with water to obtain an immobilized glucoamylase.

The overall activity yield against that of the starting native enzyme was about 70%. The glucoamylase activity was assayed similarly as in EXAMPLE 2 except that the pH of the substrate solution was adjusted to 4.5.

The product was feasible for various applications. Particularly, the immobilized glucoamylase thus obtained is suitable for producing glucose or high-sugar-content syrup, exhibiting a half life of about 300 hours at a reaction temperature of about 50° C.

EXAMPLE 5

Immobilized Pullulanase

A commercial crude Aerobacter pullulanase, produced by Hayashibara Biochemical Laboratories, Inc., Okayama, Japan, was dissolved in a 0.02 M phosphate buffer, pH 7.5, to obtain an aqueous solution having a protein concentration of 0.15 w/v %. Then to 50 ml of the solution was added 25 ml of a 0.1 w/v % dioxane solution of hexamethylene diisocyanate, and the mixture was kept at room temperature for 3 hours, and then dialyzed against water for an additonal 5 hours. The solution containing modified enzyme was added with 5 g wet weight of Diaion HP-30 and stirred gently overnight at room temperature. The resultant was washed with water to obtain an immobilized pullulanase.

The overall activity yield was about 55% against that of the starting native enzyme. In this case the enzyme activity was assayed similarly as in EXAMPLE 2.

The product was feasible for various applications. For example it is suitable for producing maltose syrup or maltose from amylaceous material, exhibiting a half life of about 300 hours at a reaction temperature of about 50° C.

EXAMPLE 6

Immobilized Isoamylase

A commercial purified Pseudomonas isoamylase, a product of Hayashibara Biochemical Laboratories, Inc., Okayama, Japan, was dissolved in a 0.1 M acetate buffer, pH 4.5, to give a protein concentration of 0.1 w/v %. To 50 ml of the solution was added 10 ml of a 0.5 w/v % aqueous glutaraldehyde solution, and the resulting solution was kept at room temperature for 2 hours, then added with 25 g wet weight of a porous glass, and stirred gently overnight at 4° C. to obtain an immobilized isoamylase.

The overall activity yield was about 65% against that of the starting native enzyme. The enzyme activity was assayed similarly as in EXAMPLE 4.

The immobilized isoamylase was feasible for various uses. For example it is suitable for producing corn syrup, glucose, high-maltose syrup or maltose, exhibiting a half life of about 200 hours at a reaction temperature of about 50° C.

EXAMPLE 7

Preparation of a Syrup Containing Oligoglucosylfructoside

Liquefaction of 20 liters of a tapioca starch slurry, 28 w/w %, was performed with a commercial liquefying enzyme NEO-SPITASE (Registered Trade Mark of Nagase & Co., Ltd., Osaka, Japan) to a D.E. of about 7.0 according to conventional method, and the liquefied starch solution was heated to 120° C. to inactivate the enzyme present in the solution, decolorized at 80° to 90° C., and filtrated. Then a substrate solution was prepared by dissolving sucrose and calcium chloride in the filtrate which had a concentration of about 24 w/w % to give a sucrose concentration of about 12 w/w % and a calcium chloride concentration of about $10^{-3}$ M.

A continuous reaction with a column system consisting of a plastic column packed with 20 g of an immobilized cyclodextrin glucanotransferase prepared by the method as described in EXAMPLE 1 was carried out by passing the substrate solution through the column at a space velocity of about 6 beds/hour, pH 6.5° and 65° C. The outlet solution was purified by decolorizing with a granule-activated-carbon-packed column and deionizing with an ion exchanger column packed with ion exchangers of H-form and OH-form.

The purified solution was concentrated under reduced pressure to give a syrup having a water content of about 20 w/w % in the yield of about 93% d.s.b.

The product was a colorless, transparent, odorless and non-crystalline syrup sweetener having a relatively high viscosity, high sweetness and mild taste. Since the predominant component of the product is oligoglucosylfructoside, it can be advantageously feasible as a low-cariogenic sweetener for foods and drinks, and improving their properties.

EXAMPLE 8

Preparation of a Powder Syrup Containing Oligoglucosylfructoside

Ten liters of a reaction mixture prepared by the method as described in EXAMPLE 7 was cooled to 50° C., and passed through a plastic column packed with 20 g of an immobilized α-amylase prepared by the method as described in EXAMPLE 2 at a space velocity of about 10 beds/hour to effect further enzymatic reaction and to lower its viscosity to about 2/3. The outlet solution was purified similarly as in EXAMPLE 7, concentrated under reduced pressure, and spray-dried to obtain a powder syrup having a moisture content of about 2 w/w % in the yield of about 90% d.s.b.

The product was a white, colorless, non-crystalline and readily water-soluble powder sweetener having a high sweetness. In addition to the above-described properties, since the predominant component of the product is oligoglucosylfructoside, the product is advantageously usable as a low-cariogenic sweetener for foods and drinks, and improving their properties.

EXAMPLE 9

Preparation of a Powder Syrup Containing Cyclodextrin

Liquefaction of 45 liters of a corn starch slurry, about 30 w/w %, was performed with acid to a D.E. of about 10 according to conventional method, and the liquefied starch solution was cooled rapidly to a temperature of about 80° to 90° C., neutralized to pH 6.0 simultaneously, then decolorized with activated carbon, and cooled to 65° C.

A continuous enzymatic reaction with a column system consisting of a stainless steel column packed with 50 g of an immobilized cyclodextrin glucanotransferase prepared by the method as described in EXAMPLE 1 was carried out by passing the above solution through the column at a space velocity of about 3 beds/hour. The outlet solution was purified, concentrated under reduced pressure, and spray-dried similarly as in EXAMPLE 8 to obtain a powder dextrin having a moisture content of about 1 w/w % in the yield of about 90% d.s.b.

The product was a white, odorless and readily water-soluble powder. Since the product contains about 20% of cyclodextrin d.s.b, it is advantageously usable as a flavour-locking agent, stabilizer, filler and vehicle for foods, drinks, flavours, cosmetics and medicines.

EXAMPLE 10

Preparation of a Powder Low-Viscosity Syrup

A substrate solution was prepared by liquefying 50 liters of a corn starch slurry, about 35 w/w %, with acid to a D.E. of about 20 according to conventional method, cooling rapidly to about 80° to 90° C., neutralizing to pH 5.0 simultaneously, decolorizing with activated carbon, and cooling to 50° C.

A continuous enzymatic reaction with a column system consisting of a stainless steel column packed with 150 g of an immobilized isoamylase prepared by the method as described in EXAMPLE 6 was carried out by passing the above solution through the column at a space velocity of about 1 bed/hour.

Analysis of the outlet solution demonstrated that the viscosity of the substrate solution decreased to about ½ by the reaction although there was a slight increase in D.E.

The outlet solution was purified, concentrated under reduced pressure, and spray-dried similarly as in EXAMPLE 8 to obtain a powder dextrin having a moisture content of about 2 w/w % in the yield of about 90% d.s.b.

The product was a white, odorless and readily water-soluble powder syrup. Since the product do not almost taste but has a low viscosity, it is advantageously usable as a stabilizer, filler and binder for foods and drinks.

EXAMPLE 11

Preparation of a Maltose Syrup

A substrate solution was prepared by liquefying 100 liters of a potato starch slurry, about 15 w/w %, with acid to a D.E. of about 4 according to conventional method, cooling to a temperature of about 80° to 90° C., neutralizing to pH 6.0 simultaneously, decolorizing with activated carbon, and cooling rapidly to 50° C.

A continuous enzymatic reaction with a column system consisting of a plastic column packed with 200 g of an immobilized $\beta$-amylase and 100 g of an immobilized pullulanase prepared by the methods as described in EXAMPLES 3 and 5 respectively was carried out by passing the above substrate solution through the column at a space velocity of about 2 beds/hour.

The outlet solution was purified and concentrated under reduced pressure similarly as in EXAMPLE 7 to obtain a transparent maltose syrup having a water content of about 25 w/w % in the yield of about 95% d.s.b.

Since the product is a syrup having a maltose content of about 83% d.s.b., and low sweetness, and being relatively liable to crystallization, it is preferable as a reduced-sweetness agent. In other words, the excessive sweetness of any foods and drinks due to excess use of sucrose can be decreased proportionally with the product to a desired sweetness without any change in their properties.

EXAMPLE 12

Preparation of a Powder Crystalline Maltose

A continuous enzymatic reaction with a column system consisting of a plastic column packed with 200 g of an immobilized $\alpha$-amylase prepared by the method as described in EXAMPLE 2 was carried out by passing 500 liters of a substrate solution prepared by the method as described in EXAMPLE 11 through the column at a space velocity of about 5 beds/hour. The reaction increased the maltose content of the solution to 86% d.s.b.

The outlet solution was purified similarly as in EXAMPLE 8, and concentrated to a water content of about 30 w/w %, and the concentrate was charged into a crystallizer, added with crystalline maltose to give a final concentration of 2%, and then cooled with agitation from 40° to 25° C. over a period of 2 days to obtain a masscuit having a crystalline maltose content of about 43% d.s.b.

The masscuit was sprayed from the top part of a drying column through a 1.5 mm-dia. nozzle, by means of a high-pressure pump at 150 kg/cm$^2$. Hot air at 85° C. was supplied from the top part of the drying column, so that the charge was collected on a moving conveyer of wire-netting located at the bottom part of the column. From below the conveyer warm air at 40° C. was blown upwardly through the conveyer, while the charge was gradually conveyed out of the drying column. The conveyer was operated at a speed that would take 40 minutes to convey the dried crystalline powder from the bottom part of the drying column to a aging column, where it was aerated with warm air for 6 hours to complete the crystallization and drying, whereby a powder crystalline maltose having a moisture content of about 6 w/w % was obtained in the yield of about 85% d.s.b.

Since the product is extremely low-hygroscopic, there was no fear of consolidation or solidification. Furthermore, the product is suitable as a reduced-sweetness agent, fermentable sugar and vehicle for foods, drinks and medicines.

What we claim is:

1. In a process for preparing immobilized starch-degrading enzyme consisting essentially of immobilizing by physical adsorption a starch-degrading enzyme onto a water-insoluble carrier, thereby insolubilizing said enzyme, the improvement whereby the activity of the enzyme after physical adsorption is enhanced, comprising, prior to the physical adsorption step, modifying or cross-linking, in solution, the starch-degrading enzyme with a mono- or poly-functional reagent at a pH in the range of 3 to 10 and temperatures in the range of 0° to 80° C., in a manner that said enzyme is not substantially insolubilized.

2. A process as set forth in claim 1, wherein said starch-degrading enzyme is α-amylase, β-amylase, glucoamylase, isoamylase, or cyclodextrin glucanotransferase.

3. A process as set forth in claim 1, wherein said modifying or cross-linking step is carried out with said starch-degrading enzyme at a concentration of 0.01 to 5 w/v%, and said mono- or poly-functional reagent at a concentration of 0.001 to 5 w/v%, for 0.1 to 50 hours.

4. A process as set forth in claim 1, wherein said reagent is selected from the group consisting of diazo compounds including bis-azo-benzidine; acid anhydrides including succinic anhydride and maleic anhydride; carboxylic acids; isocyanate compounds including hexamethylene diisocyanate and toluene 2,4-diisocyanate; isothiocyanate compounds; thioamides; imide compounds including N-acetoxy-succinimide and N,N'-ethylene-bis-maleimide; carbodiimides including 1-cyclohexyl-3-(2-morpholinoethyl) carbodiimide metho-p-toluene sulfonate; imidocarbonates; aldehyde compounds including acetaldehyde, propionaldehyde, butyraldehyde, octyl aldehyde, lauraldehyde oleyl aldehyde, benzaldehyde, p-nitrobenzaldehyde, naphthaldehyde, glyoxal, glutaraldehyde, succindiadehyde, dialdehyde starch, and dialdehyde pullulan; acetal compounds; halides including cyanuric chloride; and halosulfonyl compounds.

5. A process as set forth in claim 1, wherein said water-insoluble carrier is activated carbon, porous glass, Japanese acid clay, bleaching clay, kaolinite, alumina, silica gel, bentonite, ceramics, hydroxylapatite, calcium phosphate gel, starch, amylose, pullulan, dextran, cellulose, porous co-polymer resin, or any of their derivatives.

6. A process as set forth in claim 1, wherein said water-insoluble carrier is a porous co-polymer resin synthesized by co-polymerizing styrene monomer and one or more members of the group consisting of methyl styrene, nitrostyrene, styryl halide, acrylonitrile, vinyl acetate, vinyl chloride, divinylbenzene, butadiene, and isopurene monomers.

7. A process in accordance with claim 1, wherein said reagent is glutaraldehyde.

8. A process in accordance with claim 1, wherein said water-insoluble carrier is porous beads of styrene-divinyl benzene copolymer.

9. In a process for the production of a reaction product from amylaceous material, comprising subjecting the amylaceous material to the action of a soluble or immobilized starch-degrading enzyme, the improvement wherein the starch-degrading enzyme is an immobilized starch-degrading enzyme obtained by a process in accordance with claim 1.

10. A process as set forth in claim 9, wherein said reaction product prepared with said immobilized-starch-degrading enzyme is corn syrup, glucose, maltose, cyclodextrin, glycosylsucrose, glycosyllactose, glycosylriboflavin, glycosylesculin, glycosylrutin or glycosylstevioside.

* * * * *